(12) United States Patent
Spade et al.

(10) Patent No.: US 6,623,954 B1
(45) Date of Patent: Sep. 23, 2003

(54) PROCESS FOR REMOVAL OF PHOSPHOROUS FROM A DAIRY STREAM

(75) Inventors: Michael Eugene Spade, Fairless Hills, PA (US); Jonathan Kim Weil, Lansdale, PA (US); Michael Scott McHale, Willow Grove, PA (US)

(73) Assignee: Neose Technologies, Inc., Horsham, PA (US)

( * ) Notice: Subject to any disclaimer, the term of this patent is extended or adjusted under 35 U.S.C. 154(b) by 0 days.

(21) Appl. No.: 10/157,255

(22) Filed: May 28, 2002

(51) Int. Cl.$^7$ .............................. C12S 3/02; A23C 21/02
(52) U.S. Cl. .................... 435/274; 435/105; 435/99; 435/72; 435/168; 435/267; 435/268; 426/34; 426/41; 426/42
(58) Field of Search ................................ 435/274, 105, 435/99, 72, 168, 267, 268; 426/42, 41, 34

(56) References Cited

U.S. PATENT DOCUMENTS 5,939,303 A * 8/1999 Cheng et al. ............... 435/196
6,139,892 A * 10/2000 Fredlund et al. ............ 426/458

OTHER PUBLICATIONS

Andersson et al. 1996, J. Infect. Disease 153:232–237.
Ayers et al. 1986, New Zealand J. Dairy Science and Technology 21:21–35.
DeWitt et al. 1986, Neth. Milk Dairy J., 40:41–56.
Gardiner 2000, GlycoScience 1:1–2.
Gronberg et al. 1989, Carbohydrate Research 191:261–278.
Heine et al. 1993, Monatsschr. Kinderheild., 141:946–950.
Holmgren et al. 1983, Infection and Immunity 39:147–154.
Horwood et al. 1998, Pediatrics, 101:1–7.
Idota et al. 1995, Biosci. Biotech. Biochem., 59:417–419.
McVeagh et al. 1997, J. Paediatr. Child Health, 33:281–286.
Mechref et al. 1999, Glycobiology, 9:227–234.
Sanchez–Diaz et al. 1997, J. Pediatric Gastroenterology Nutr. 28:405–410.
Schwertzmann, 1999, J. Pediatric Gastroenterology Nutr. 28:257–263.
Tram et al., 1997, Arch. Disease Child., 77:315–318.
Trugo et al., 1988, Braz. J. Med. Biol. Res., 21:883–894.

* cited by examiner

*Primary Examiner*—Francisco Prats
(74) *Attorney, Agent, or Firm*—Morgan, Lewis & Bockius, LLP

(57) ABSTRACT

The invention relates to a method of removing phosphorous from sialyloligosaccharides isolated from a dairy stream using phytase.

16 Claims, 1 Drawing Sheet

PROCESS FOR REMOVAL OF PHOSPHOROUS FROM A DAIRY STREAM

BACKGROUND OF THE INVENTION

This invention relates to a method of reducing phosphate levels in a dairy stream.

A non-limiting use of sialyloligosaccharides is in infant formula. While natural human milk is widely regarded as the highly preferred source of nutrition for infants, many reasons and conditions exist that prevent mothers from feeding their infants in this manner. These reasons include abnormal levels of hormones that regulate the lactation process, such as estrogen, prolactin, and oxytocin, breast surgeries that prevent or inhibit breastfeeding, such as biopsies, lumpectomies, and mastectomies, and the presence of infectious organisms that might be passed from mother to child, including hepatitis C virus, human immunodeficiency virus, and herpes simplex viruses. Furthermore, many drugs, including those used in radiation therapy and chemotherapy for treating various cancers cannot be used in conjunction with breastfeeding for fear that they may be passed to the infant in breast milk. In addition, some mothers may choose not to breastfeed their children due to time constraints or personal choice. In these cases, synthetic infant formula is the only viable option to human milk.

Natural human milk is a complex mixture that includes primarily proteins, lipids, antibodies, and oligosaccharides. Approximately 130 oligosaccharides have been identified in human milk (McVeagh et al., 1997, J. Paediatr. Child Health, 33:281–286). The benefits of human milk are well documented and have been shown to confer immunity to infectious diseases from mother to child through secretory IgA, and to provide complete nutrition and essential glycoconjugates for nervous, digestive, and cognitive development (Gardiner, 2000, GlycoScience, 1:1–10). Oligosaccharides present in human milk have been shown to prevent cell adherence of *V. cholerae, S. pneumoniae, E. coli*, and *H. influenzae* (Holmgren et al., 1983, Infect. Immun., 39:147–154; Andersson et al., 1986, J. Infect. Dis., 153:232–237; Schwertzmann, 1999, J Pediatr. Gastroenterol. Nutr., 28:257–263; Idota et al., 1995, Biosci. Biotechnol. Biochem., 59:417–419). Of the necessary glycoconjugates in human milk, sialic acid containing oligosaccharides are some of the most prominent (Gronber et al., 1989, Carbohydr. Res. 191:261–278). Sialic acid containing glycoconjugates increase the bioavailability of vitamin $B_{12}$, and are necessary for fat metabolism (Trugo, 1988, Braz. J. Med. Biol. Res., 21:883–894; Mechref et al., 1999, Glycobiology, 9:227–234). Sialyloligosaccharides have been shown to be vital components of cell membranes and membrane-bound receptors, as well as being necessary for normal brain development (Heine et al., 1993, Monatsschr. Kinderheilkd., 141:946–950). Additionally, a sialic acid supplemented diet has been correlated with increased learning behavior in mammals (Tram et al., 1997, Arch. Dis. Child., 77:315–318).

In light of the numerous previously mentioned hindrances to natural breastfeeding, and the importance of human milk to the health and development of infants, synthetic infant formulas have been developed. Although many efforts have been made to adequately reproduce all of the benefits of human milk in synthetic infant formula, long term studies have established that increased academic and cognitive abilities exist in children who were breastfed versus those who were fed infant formula (Horwood et al., 1998, Pediatrics, 101:1–7). This finding illustrates two facts. The first is that synthetic infant formulas do not yet approach parity with human milk. The second is that given the importance of sialyloligosaccharides in neurological development, infant formulas are obviously lacking when it comes to providing important sialyloligosaccharides for neurological development. Infants fed synthetic infant formula demonstrate physiological levels of sialyloligosaccharides and other sialic acid containing glycoconjugates that are 64% to 80% lower than infants fed breast milk (Sanchez-Diaz et al., 1997, J. Pediatr. Gastroenterol. Nutr., 27:405–410). Therefore, the need exists for a method of increasing the sialyloligosaccharide content of synthetic infant formulas.

Existing methods for enriching a dairy stream for sialyloligosaccharides result in relatively low yields of sialyloligosaccharides and a high phosphorous content in the product. Highly phosphorylated foodstuffs are poorly digested, can decrease the absorption of calcium and iron, complex with other divalent cations necessary for normal physiological processes, and inhibit the action of gastrointestinal enzymes. In the case of sialyloligosaccharides as a supplement to infant formula, the existing problem with foodstuffs having a high phosphate content may negate any added benefit of additional sialyloligosaccharides.

The total phosphate content of human milk ranges from approximately 150 mg/L to 240 mg/L, whereas the total phosphate content of many existing infant formulas, both those based on either bovine milk or soy milk, often exceed this range by more than two-fold. Given the previously noted problem with foods having a high phosphate content, it is apparent that there is a need to enhance the sialyloligosaccharide content of infant formula while simultaneously reducing phosphate levels. Existing methods are not capable of meeting these requirements.

A source of sialyloligosaccharides to supplement synthetic infant formula is whey, and its by-product, DeLactose Permeate (DLP). Whey is a major by-product of cheesemaking which for environmental reasons, presents a difficult waste disposal problem. Whey is typically composed of about 5% by weight lactose, 1% by weight protein and about 0.5% by weight salts, where the balance of the mixture is water. DLP is produced by the ultrafiltration of whey to produce whey permeate followed by lactose crystallization resulting in DLP. While the protein component can often be recovered by ultra-filtration and accordingly used in food products, the remainder of the dairy waste stream has heretofore been of little value.

The isolation of sialyloligosaccharides is one method of increasing the economic and nutritional value of whey waste streams. Anion exchange chromatography is effective for removing charged sialyloligosaccharide components from lactose. The presence of salts, especially citrate salts from acid addition, can greatly reduce the effectiveness of sialyloligosaccharide removal such that it is conventional to remove salts from a whey waste stream in order to achieve effective recovery of sialyloligosaccharides.

Methods for removing sialyloligosaccharide fractions from a dairy stream have been reported, but the extraction and ion exchange methods have not been entirely satisfactory from the standpoint of throughput and purity. Furthermore, the low yield and high phosphorous content of sialyloligosaccharides isolated from a dairy stream thus far have made them unsuitable for use as a supplement to synthetic infant formula.

There is a long felt need for a method to isolate sialyloligosaccharides that comprises a high yield of product having a low phosphate content. The present invention meets these needs.

SUMMARY OF THE INVENTION

The invention relates to a method of processing a dairy stream comprising contacting a dairy stream with a phytase enzyme, wherein the dairy stream comprises lactose and sialyloligosaccharides.

In one embodiment, the sialyloligosaccharide is isolated after treatment of the dairy stream with a phytase.

In another embodiment, the lactose is hydrolyzed with a β galactosidase enzyme. In one aspect of this embodiment, the dairy stream is contacted by β galactosidase and phytase in the same step. In another aspect of this embodiment, the dairy stream is contacted by β galactosidase and phytase in separate steps.

The invention also relates to a method of preparing a sialyloligosaccharide-containing composition of a dairy stream, the method comprising hydrolyzing a lactose component of a dairy stream comprising lactose and a sialyloligosaccharide, contacting the dairy stream with phytase, and isolating a sialyloligosaccharide containing component, thereby preparing the sialyloligosaccharide containing component.

In one embodiment, the steps of hydrolyzing lactose, contacting the dairy stream with phytase, and isolating a sialyloligosaccharide component are performed in any order, provided that isolating the sialyloligosaccharide component is preceded by contacting the dairy stream with phytase.

In still another embodiment, the hydrolyzing of lactose is conducted with a β galactosidase enzyme.

In one embodiment of the invention, the sialyloligosaccharide component comprises a sialyloligosaccharide selected from the group consisting of 3' sialyllactose, 6' sialyllactose, 6' sialyllactosamine, 3' sialyllactosamine, disialyllactose, and a mixture thereof.

In another embodiment, the phytase is immobilized on a support.

In yet another embodiment, the phytase is in an aqueous medium.

In one embodiment of the invention, the sialyloligosaccharide component is isolated by membrane filtration. In another aspect of this embodiment, the membrane filtration is nanofiltration.

The present invention also relates to a method of producing a glucose and galactose containing composition from a dairy stream wherein the method comprises hydrolyzing a lactose component of a dairy stream comprising lactose and a sialyloligosaccharide, contacting the dairy stream with phytase, and isolating a glucose and galactose containing component, thereby preparing a glucose and galactose containing composition.

In one aspect of the present invention, the glucose and galactose containing composition comprises glucose and galactose in a ratio of about 0.95 to 1.05:1

In another aspect of the present invention, the glucose and galactose containing composition is isolated by membrane filtration.

In yet another aspect of the present invention, the membrane filtration is nanofiltration.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise embodiments shown. In the drawings.

DETAILED DESCRIPTION OF THE INVENTION

Figure 1:
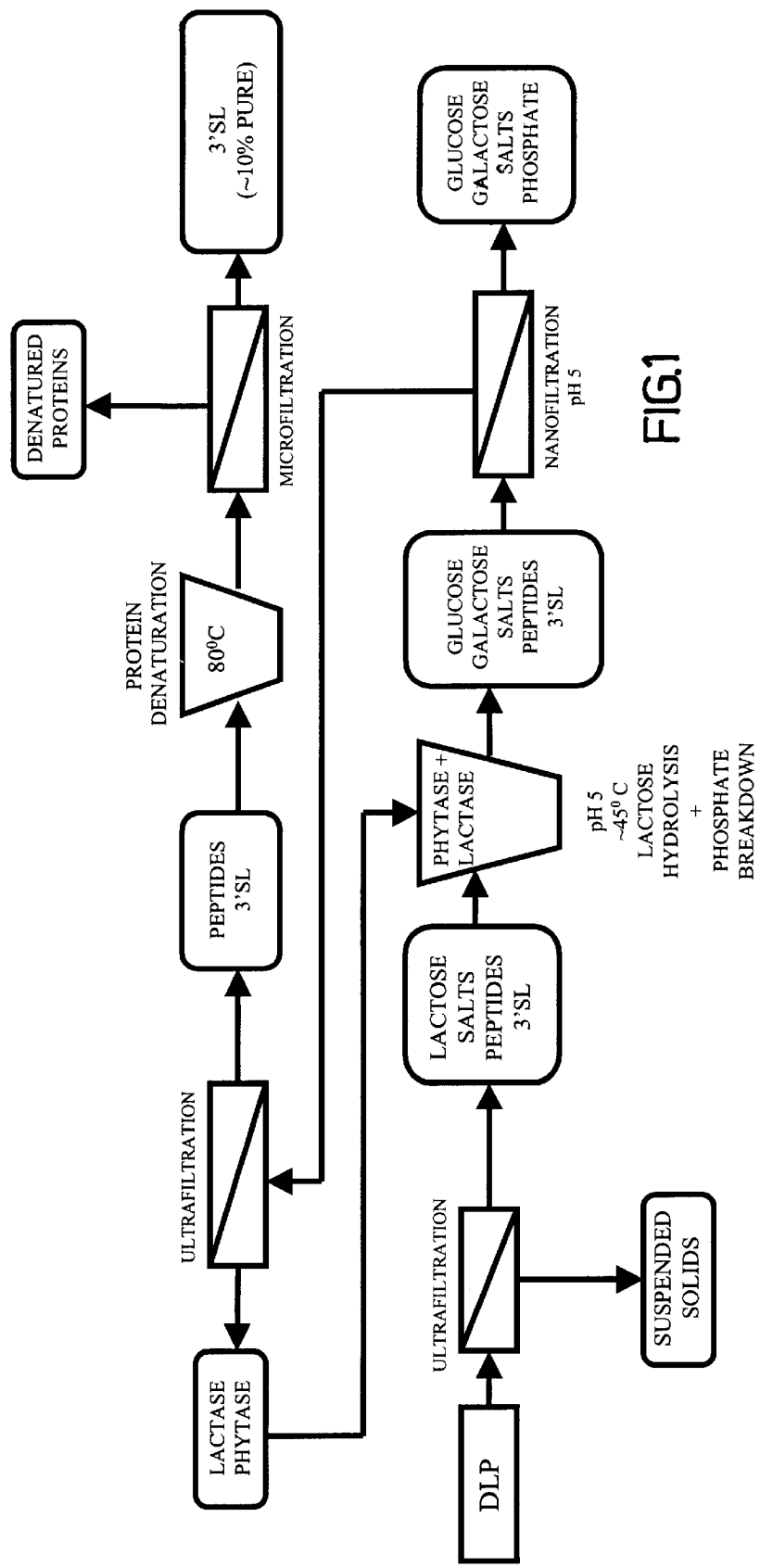
FIG. 1 is a schematic representation of an example of the process to remove phosphorous from the sialyloligosaccharide fraction of a dairy stream. A dairy stream is filtered through an ultrafiltration membrane to remove some portion of the fats, proteins, and non-oligosaccharide components of a dairy stream. The filtered stream is then contacted with phytase and P galactosidase enzymes where the temperature and pH are adjusted to facilitate the hydrolysis of lactose and dephosphorylation of phosphorylated compounds. The dairy stream is then filtered through a nanofiltration membrane to remove impurities and end products of the enzymatic reactions while retaining the sialyloligosaccharide fraction. The phytase and β galactosidase enzymes can be retained for reuse at this point in the process, if desired, by filtering the sialyloligosaccharide through an ultrafiltration membrane. Finally, the dairy stream is heated to precipitate excess proteins and/or peptides and filtered through a microfiltration membrane to remove remaining non-oligosaccharide components. This process results in a product comprising approximately 0.1%–30% by weight 3' sialyloligosaccharides.

The present invention is based in-part on the discovery that sialyloligosaccharides are more easily separated when separation is conducted on a waste stream from which lactose has been hydrolyzed to glucose and galactose and the sialyloligosaccharide fraction is enriched and dephosphorylated by contacting the sialyloligosaccharide fraction with phytase. The resulting product, a sialyloligosaccharide containing composition, comprises a higher percent of sialyloligosaccharides useful in cosmetics, pharmaceutical compositions, foods, and infant formulas.

The main activity of phytase enzymes is to release orthophosphate from phytate in plant matter. Phytate is not commonly known to be found in dairy streams, but as has been discovered in the present invention, phytase is capable of liberating orthophosphate from phosphorylated compositions found in dairy streams.

A dairy stream may be processed essentially as described in Roth et al. (U.S. Pat. No. 6,288,222), except that the order of the steps shown may be changed and critical to the present invention, is the addition of phytase to at least one of the several steps in the process.

Within the context of the present invention a sialyloligosaccharide includes but is not limited to 3' sialyllactose, 6' sialyllactose, 6'sialyllactosamine, 3' sialyllactosamine and disialyllactose.

A method, according to the present invention, for preparing a high yield of sialyloligosaccharides with a low phosphate content may proceed as follows. The source of the composition for purification is a dairy stream (FIG. 1). The dairy stream may be filtered to remove salts, fats, protein, peptides, or other suspended solid waste, or the dairy stream may be filtered at a later step in the process. The enzymes, lactase or β galactosidase, and phytase are also added to the dairy stream to hydrolyze lactose into glucose and galactose and remove phosphate groups. These enzymes may be added before or after filtration and may be added together or at different times. The pH and temperature of the dairy stream may be adjusted to facilitate the preferential hydrolysis of lactose over sialyloligosaccharides, the removal of phosphate groups, and the catalytic action of the enzymes. The pH and temperature may be adjusted before, after or during the addition of β galactosidase and phytase. The dairy stream may then be filtered again to separate the sialyloligosaccharide component from the hydrolyzed lactose and phosphate components as well as other compounds, or filtration may be conducted at a step earlier or later in the process. The separated sialyloligosaccharide component may then be heated and filtered to denature proteins and further separate sialyloligosaccharides from other components of the dairy stream. Heating and filtration may be conducted as an earlier or later step in the process. The final product may be filtered again to remove any traces of enzymes, and to recover the enzymes for further use. The filtration may be conducted at an earlier or later step in the process.

Filtration of a hydrolyzed dairy stream may be conducted when the waste stream comprises sialyloligosaccharides and lactose. However, most dairy streams contain additional components other than oligosaccharides such as proteins, salts and fats, and accordingly their removal may be accomplished by conventional methods known to those of ordinary skill in the art.

A nanofiltration membrane may be used in the filtration step where the nanofiltration membrane can be a reverse osmosis membrane having a molecular weight cut off of about 1000 Daltons. A non-limiting example of a membrane is a G5 membrane, manufactured by Desal (Rochdale, Lancashire, UK). Nanofiltration is conducted at a positive pressure of from 10 to 1,000 lbs/psi, preferably 50 to 800 lbs/psi, more preferably 100 to 400 lbs/psi. The temperature of nanofiltration is not particularly limited and may be conducted from about 10° C. to about 50° C. At low pH and high temperature the sialyloligosaccharide will begin to degrade. The size (surface area) of the nanofiltration membrane may be selected as appropriate by those of skill in the art, depending on the volume of dairy stream being treated, the concentration of material in the solution being nanofiltered and the desired throughput.

After obtaining an oligosaccharide containing fraction from the dairy stream, sialyloligosaccharides may be further purified by hydrolysis of lactose and subsequent separation of the sialyloligosaccharides therefrom.

There is no particular limitation to the method used to hydrolyze lactose in the waste stream to be processed. Treatment of the dairy stream with a hydrolytic enzyme selective for the cleavage of the glucose-galactose linkage of lactose is preferred. The extent of a hydrolysis treatment shall be sufficient to hydrolyze lactose to the monosaccharides glucose and galactose without significantly hydrolyzing the sialyloligosaccharide component.

Preferably, hydrolysis is conducted under conditions such that the ratio between the rate of hydrolysis of lactose to the rate of hydrolysis of sialyloligosaccharide is >10:1, more preferably >15:1, even more preferably >20:1, more preferably >500:1 and even more preferably >50,000:1.

In one embodiment, hydrolysis is catalyzed by an enzyme, particularly a β galactosidase or lactase enzyme. A suitable β galactosidase or lactase enzyme may be obtained by conventional methods known to those of ordinary skill in the art without undue experimentation. In a preferred embodiment, a β galactosidase is generated by fermentation of Aspergillus oryzae. In another embodiment, lactase is derived from Lactobacillus acidophilus. Suitable enzymes may be obtained from Enzyme Development Corp. of New York. Suitable enzymes are also available as LACTAID® from McNeil Nutritionals (Fort Washington, Pa.).

Typically enzymatic hydrolysis is conducted in an aqueous medium, such as water, which may further comprise additional components known to those of ordinary skill in the art.

The pH of the dairy stream may be adjusted by conventional methods known to those of ordinary skill in the art in order to maximize the differentiation in hydrolysis rate of lactose relative to sialyloligosaccharides. For example, a pH of from about 3 to about 8, preferably from about 4 to about 7, more preferably about 5.5 may be chosen. The desired pH range may be obtained by adding a protonic acid such as HCl, $H_2SO_4$, HOAc, oxalic acid, citric acid or lactic acid to the hydrolysis reaction. If necessary the pH may also be adjusted by adding a suitable base to the reaction medium, such as NaOH, $NaHCO_3$, or ammonia. The reaction medium may be buffered in order to adjust the pH to the optimum activity of the cleavage of the glucose-galactose bond. Suitable buffers may-be selected by those of ordinary skill in the art. However, from the perspective of minimizing the ionic strength of the reaction medium, a buffer with high capacity is preferable.

The amount of enzyme used to effect hydrolysis of the dairy stream is not particularly limited and may be selected in order to obtain cost efficient and time efficient hydrolysis for a given enzyme of a given activity. For examples, 4,500 activity units of a β galactosidase are effective to hydrolyze >99% of a solution containing 0.45 g of lactose in about one hour, where an activity unit will hydrolyze 1 micromole (342 μg) of lactose in one minute. Acceptable rates of hydrolysis are observed with as little as 40 activity units acting on 0.45 g of lactose.

The reaction temperature is not particularly limited and may be selected to obtain cost and time efficient hydrolysis. The temperature is typically about 10° to 55° C., preferably about 20° to about 40° C., more preferably about 25° to about 38° C., more preferably about 37° C. While there is no loss of selectivity observed at the high end of the temperature range, the combination of high temperature and low pH (a pH of about 2) can result in degradation of sialyloligosaccharides and β galactosidase enzyme.

After hydrolysis of the lactose component of the dairy stream, separation of the hydrolyzed material into a sialyloligosaccharide containing fraction and a glucose/galactose containing fraction may be performed.

Separation of the sialyloligosaccharide component from the hydrolyzed dairy stream may be accomplished by conventional methods known to those of ordinary skill in the art such as by filtration (nanofiltration and ultrafiltration, crystallization and chromatography).

Separation may be accomplished by nanofiltration through a membrane and separation based on molecular weight and/or charge. For example, a suitable membrane is Desal GE sheet membrane spiral wound, ceramic, polyether sulfone, polyvinyl difluoride and regenerated cellulose. Typical membrane selectivity under general conditions will be >50:1, preferably >75:1, more preferably >100:1, even more preferably >500:1, in selecting glucose and galactose over a sialyloligosaccharide.

Nanofiltration conditions may be selected by those of ordinary skill in the art to produce an acceptable level of separation at an acceptable rate. Adjustment of pressure (typically 10 to 1,000 psig, preferably 200–400 psig), temperature (typically about 10 to about 60° C., preferably about 25 to about 38° C.) and flow rate is sufficient to obtain acceptable levels of separation. The pH is not particularly limited; however at a pH below 3, sialyllactose is typically passed through the membrane.

In a preferred embodiment, the resulting sialyloligosaccharide containing component has an enrichment of sialyloligosaccharide to lactose of about >50:1, preferably about >75:1, more preferably about >100:1, even more preferably about >500:1, relative to the oligosaccharide component prior to hydrolysis.

The retentate after nanofiltration may have a residual lactose content of about $\leq 50\%$ by weight, preferably about $\leq 20\%$ by weight, more preferably about $\leq 10\%$ by weight, more preferably about $\leq 5\%$ even more preferably about $\leq 0.5\%$ by weight. The retentate after nanofiltration may have a residual combined glucose and galactose content of about $\leq 5\%$ by weight, preferably about $\leq 3\%$ by weight, more preferably about $\leq 1\%$ by weight, even more preferably $\leq 0.5\%$ by weight.

The dairy stream which is processed according to the present invention, may be obtained from any waste stream generated during a cheese making process. For example acid whey is generated by separating the solids when skim milk is coagulated to form cottage cheese. Whey is a suitable hydrolysis medium as it is typically acidic due to the action of lactic acid producing bacteria on lactose. Acid whey is characterized by having a high lactic acid content. When cheese is prepared from whole milk, the remaining liquid is sweet whey which can be further processed by evaporation to form dry whey powder. Sweet whey can also be dried, demineralized and evaporated to form demineralized whey permeate. Sweet whey can also be subjected to ultrafiltration to generate both a whey permeate and a whey permeate concentrate. Whey permeate can be further processed by crystallizing lactose to form both lactose and a mother liquor. The mother liquor resulting from crystallizing lactose from a whey permeate is known in the art as DLP or "Delac". Suitable dairy streams include colostrum, milk, milk powder, whole whey, demineralized whey permeate, the regeneration stream from demineralized whey permeate, whey permeate, crystallized lactose, spray dried lactose, whey powder, edible lactose, lactose, refined lactose and USP lactose. Preferably the aqueous mother liquor material resulting from crystallizing lactose (i.e. DLP) is used.

Prior to removal of a sialyloligosaccharide fraction, the dairy stream may be processed to enhance the content of sialyloligosaccharides. For example, a dairy stream which still contains a protein fraction may be treated with a trans-sialidase enzyme, which increases the concentration of sialyloligosaccharides, by transferring sialic acid groups from a sialylated protein, to lactose. A suitable trans-sialidase enzyme is available from Trypanosome species. Suitable reaction conditions for trans-sialidase are a temperature of from 25 to 40° C., preferably about 37° C., at an enzyme concentration of 500 units/Liter, and a solute concentration of 5–10 wt. %, preferably about 7 wt. % and a pH of about 4–11, preferably about 6.

Fluid cheese permeate is typically dried so as to produce a non-hygroscopic, highly dispersible powder. Fresh fluid whey is clarified by passing through a desludging type clarifier. The whey is separated to remove fat, then concentrated in double or triple effect evaporators to a solids content of about 62% by weight. The solids can be removed by separation at room temperature or more preferably, the concentrated whey is cooled before the solids are removed.

When the dairy stream to be processed is the solids obtained from drying whey, the solids are first dissolved in water, preferably in an amount of about 1 to 620 g, preferably about 50 to 200 g, more preferably about 100 g of solids per liter of water. Dissolution of the solids obtained from drying cheese whey can be conducted at room temperature or at elevated temperatures to accelerate the dissolution process and increase the amount of dissolved solids. Preferably, temperatures of from about 200 to about 80° C. are suitable.

Any technique known to those of ordinary skill in the art can be used to remove positively charged materials. For example one suitable technique for causing whey protein to be absorbed is by contacting with a cation exchange resin, (DeWitt et al., Neth. Milk Dairy J., 40:41–56, 1986; Ayers et al. New Zealand J. Dairy Sci. & Tech., 21:21-35, 1986), as well as those processes described in JP 52-151200 and 63-39545 and JP 2-104246 and 2-138295.

Suitable cation exchange resins may be prepared by conventional techniques known to those of ordinary skill in the art. For example a suitable cation exchange resin may be produced from a mixture of polymerizable monofunctional and polyfunctional monomers using radical emulsion polymerization techniques, then the resin is functionalized with acidic groups such as carboxylic acid groups or sulfonic acid groups that exist in the protonated form.

The degree of cross-linking in the cation exchange resin can be chosen depending on the operating conditions of the cation exchange column. A highly cross-linked resin offers the advantage of durability and a high degree of mechanical integrity; however it suffers from a decreased porosity and a drop off in mass-transfer. A low-cross-linked resin is more fragile and tends to swell by absorption of mobile phase. A suitable resin may have from 2 to 12% cross-linking, preferably 8% cross-linking.

The particle size of the cation exchange resin is selected to allow for efficient flow of the dairy stream while still effectively removing the positively charged materials. A suitable particle size for a column 30×18 cm is 100–200 mesh.

Suitable cation exchange resins include but are not limited to CM-Sephadex, SP-Sephadex, CM-Sepharose, S-Sepharose, CM-Cellulose, Cellulose Phosphate, Sulfoxyethyl-Cellulose, Amberlite, Dowex-SOW, Dowex HCR-S, Dowex Macroporous Resin, Duolit C433, SP Trisacryl Plus-M, SP Trisacryl Plus-LS, Oxycellulose, AG 50W-X2, AG50W-X4, AG50W-X8, AG50W-X12. AG 50W-X16, AG MP-50 Resin, Bio-Rex 70. More preferably suitable resins are DOWEX.TM. 50×8 (an aromatic sulfonic acid linked to a polystyrene crosslinked resin from Dow Chemical) and AMBERLYST.TM.-15, AMBERLITE.TM. IR-120 AND AMBERLITE.TM.-200 acidic resins.

The dairy stream can be contacted with the cation exchange resin in any suitable manner which would allow the whey proteins and other positively charged materials to be absorbed onto the cation exchange resin. Preferably the cation exchange resin is loaded onto a column and the dairy stream is passed through the column to remove the whey proteins. An amount of cation exchange resin is selected to affect removal of the positively charged materials and will vary greatly depending on the dairy stream being treated. Typically, when the waste stream is whey permeate, the loading ratio of dairy stream to cation exchange resin may be from about 5 to about 20, preferably from about 8 to about 15, more preferably from about 9 to about 12:1 v/v.

When contacting is effected in a column, the dairy stream is preferably passed at a rate of from 1 to 70 cm/min, preferably from 2 to 15 cm/minute, more preferably at a rate of 4.6 cm/minute. A suitable pressure may be selected to obtain the desired flow rate. Typically a pressure of from 0 to 100 psig is selected. Suitable flow rates may also be obtained by applying a negative pressure to the eluting end of the column, and collecting the eluent. A combination of both positive and negative pressure may also be used.

The temperature used to contact the dairy stream with the cation exchange resin is not particularly limited as long as the temperature is not too high to cause decomposition of the components of the waste stream. Generally ambient room temperature of from 17 to 25° C. is used.

Alternatively, the positively charged materials can be removed using such techniques as electrophoresis, ultrafiltration, reverse osmosis or salt precipitation.

Reverse osmosis is preferably conducted at a pressure of from about 300 to about 1,600 psi, more preferably from about 400 to about 600 psi, even more preferably at a pressure of about 450 psi.

After the salts have been removed by reverse osmosis, the resulting material can be concentrated to provide a solid material containing sialyloligosaccharides such as 3' sialyllactose and 6' sialyllactose, which can be recrystallized from a mixture of water and organic solvents.

Preferably, precipitation solvents are selected from the group consisting of ethanol, acetone, methanol, isopropanol, diethyl ether, t-butyl methyl ether, ethyl acetate, hexane, tetrahydrofuran and water.

In addition, the eluent from the anion exchange column which contains a mixture of sialyloligosaccharides that includes 3' sialyllactose, 6' sialyllactose and 6' sialyllactosamine can be subjected to separation of the sialyloligosaccharides contained therein by column chromatography on a DOWEX 1×2 anion exchange resin at pH 4 to 6 using a buffer a suitable salt such as sodium acetate, ammonium acetate or a lithium salt such as lithium acetate, lithium perchlorate, lithium chloride and lithium bromide as an eluent. A solution of lithium acetate is preferred.

Suitable anion exchange resins may be prepared by conventional techniques known to those of ordinary skill in the art as previously described.

The degree of crosslinking in the anion exchange resin can be chosen depending on the operating conditions of the anion exchange column. A suitable resin may have from 2 to 12% crosslinking, preferably about 2% cross-linking.

The particle size of the anion exchange resin is selected to allow for efficient flow of the daily stream while still effectively affecting chromatographic separation of the negatively charged materials. A suitable particle size for a column 20×100 cm is 200–400 mesh.

Suitable anion exchange resins include but are not limited to DEAE Sephadex, QAE Sephadex, DEAE Sepharose, Q Sepharose, DEAE Sephacel, DEAE Cellulose, Ecteola Cellulose, PEI Cellulose, QAE Cellulose, Amberlite, Dowex 1-X2, Dowex 1-X4, Dowex 1-X8, Dowex 2-X8, Dowex Macroporous Resins, Dowex WGR-2, DEAE Trisacryl Plus-M, DEAE Trisacryl Plus-LS, Amberlite LA-2, AG 1-X2, AG 1-X4, AG 1-X8, AG 2-X8, AG MP-1Resin, AG 4-X4, AG 3-X4, Bio-Rex 5 and ALIQUAT-336 (tricaprylylmethylammonium chloride from Henkel Corp. (Dusseldorf, Germany). Preferred resins are DOWEX 1×2 (a tri-methylbenzyl ammonium linked to a polystyrene crosslinked resin from Dow Chemical (Midland, Mich.)) and AMBERLYST and AMBERLYTE basic resins.

The mixture of sialyloligosaccharides to be separated are subjected to column chromatography on an anion exchange resin. An amount of anion exchange resin is selected to affect separation of the different sialyloligosaccharides. Typically the loading ratio of sialyloligosaccharide to anion exchange resin is from about 0.1 to about 5, preferably from about 0.2 to about 4, more preferably about 1 gram of material per liter of resin at a loading concentration of from about 0 to about 10 mM of salt. The chromatography is conducted at a rate of from about 1 to 20 cm/hour, preferably 4.6 cm/hour superficial velocity. A suitable pressure may be selected to obtain the desired flow rate. Typically a pressure of from 0 to 22 psig is selected. Suitable flow rates may also be obtained by applying a negative pressure to the eluting end of the column and collecting the eluent. A combination of both positive and negative pressure may also be used.

Any temperature may be used to contact the dairy stream with the anion exchange resin as long as the temperature is not too high to cause decomposition of the components of the sialyloligosaccharides. Generally ambient room temperature of from about 17 to about 25° C. is used.

When the buffer eluent is a lithium salt, the individual sialyloligosaccharides can be isolated by concentrating the eluent to form a solid and washing the lithium salts away with an organic solvent. Isolation of the lithium salt of a sialyloligosaccharide from a lithium salt eluent is as previously described herein.

The sodium salt of the sialyloligosaccharide can be obtained by conventional ion-exchange techniques, known to those of ordinary skill in the art.

When the buffer eluent is not a lithium salt, the individual sialyloligosaccharides can be isolated by reverse osmosis techniques.

The present invention is also directed to a method of simultaneously enriching a dairy stream for sialyloligosaccharides and removing phosphorus from the sialyloligosaccharides.

For example, the dairy stream may be enriched for sialyloligosaccharides and phosphate may be liberated from the sialyloligosaccharide mixture by treatment with phytase followed by nanofiltration.

There is no particular limitation to the method used to dephosphorylate sialyloligosaccharides. Treatment with a phytase capable of liberating phosphate from the sialyloligosaccharide compound is preferred. Phytase treatment is sufficient if it liberates orthophosphate from the sialyloligosaccharide component.

Within the context of the current invention, a phytase will include, but is not limited to 3-phytase, 6-phytase, or a mixture thereof.

In a preferred embodiment, dephosphorylation is catalyzed by phytase. A suitable phytase enzyme may be obtained by conventional methods known to those of ordinary skill in the art, without undue experimentation. In a preferred embodiment, phytase is made from fermentation of Aspergillus. In another preferred embodiment, phytase is made genetically modified Trichoderma reesei. Phytase may also made by other recombinant organisms capable of producing an enzyme with phytase activity. Suitable phytase enzyme may be obtained from BASF as NATUPHOS® or Enzyme Development Corporation as ENZECO®. Additionally, compositions comprising phytase enzyme are disclosed in U.S. Pat. Nos. 6,110,719; 6,060,298; 6,054,306; 6,039,942; 6,033,897, 5,863,533; 5,827, 709; 5,939,303; 5,876,997; 5,840,561; 5,830,732; 5,443,979;

In one embodiment, enzymatic dephosphorylation is conducted in an aqueous medium such as water which may further comprise additional components well known to those of ordinary skill in the art.

In another embodiment, enzymatic dephosphorylation is conducted with the phytase immobilized on a support which may further comprise additional components well known to those of ordinary skill in the art.

The pH of the sialyloligosaccharide containing dairy stream may be adjusted to accomplish the most efficient enzymatic dephosphorylation of sialyloligosaccharides. For example, a pH of from about 3 to about 8, preferably from about 4 to about 7, more preferably about 5.0–5.5. The desired pH may be obtained by the addition of an acid such as HCl, $H_2SO_4$, acetic acid, oxalic acid, citric acid, or lactic acid.

If necessary, the pH of the reaction mixture may also be adjusted by adding a suitable base such as NaOH, $NaHCO_3$, or ammonia.

The reaction may be buffered in order to achieve the most efficient enzymatic dephosphorylation of sialyloligosaccharides. Suitable buffers will be obvious to those of ordinary skill in the art.

The amount of enzyme used for enzymatic dephosphorylation is only limiting in that a suitable amount is used to obtain time and cost efficient dephosphorylation. In one embodiment, about 100,000 units of enzyme are used per gram of oligosaccharide. In another embodiment, about 500 units to about 500,000 units of enzymes are used per liter of DLP. The amount of enzyme to be used in relation to the amount dairy stream to be processed will be readily apparent to one of ordinary skill in the art.

The reaction temperature is limited only to obtain time and cost efficient enzymatic dephosphorylation and is preferably about 20 to about 70° C., more preferably about 30 to about 60° C., yet more preferably about 50° C. The reaction may be conducted at a pH of about 2 to about 7, more preferably at a pH of about 3 to about 6, even more preferably at a pH of about 5.5. One of ordinary skill in the art will be able to determine the proper temperature for the most efficient enzymatic dephosphorylation with a caveat that low pH and high temperature can result in degradation of both sialyloligosaccharides and enzymes.

Once dephosphorylation of the sialyloligosaccharide containing component of the dairy stream is accomplished, separation of the sialyloligosaccharides component from the orthophosphate component can be accomplished by conventional methods known to those of ordinary skill in the art. Conventional methods include, but are not limited to filtration, nanofiltration, ultrafiltration, crystallization, and chromatography.

For examples, the dephosphorylated sialyloligosaccharide fraction may be separated from the orthophosphate fraction by filtration, or by other methods known to those of ordinary skill in the art.

In a preferred embodiment, separation may be by nanofiltration through a membrane, selecting by molecular weight. A suitable membrane may be a spiral, thin-film, flat sheet, or hollow fiber membrane, and may comprise polysulfone, cellulose, or other materials well known to those of ordinary skill in the art. A suitable membrane is a Desal Osmonics GE membrane with a molecular weight cutoff of 1000 Daltons. Typical membrane selectivity will be about >50:1, preferably about >75:1, more preferably about >100:1, even more preferably about >500:1, and most preferably about >1000:1 in selecting sialyloligosaccharides over orthophosphate.

Nanofiltration is conducted at a positive pressure of about 10–1000 lbs/psi, more preferably about 100–500 lbs/psi, more preferably about 200–400 lbs/psi, most preferably about 350 lbs/psi.

The temperature at which the nanofiltration is conducted is not particularly limited, and may be conducted at about 10–50° C., depending on the filtration apparatus used, again with the caveat that high temperature may lead to the degradation of sialyloligosaccharides.

The surface area of the nanofiltration membrane selected will be obvious to those of ordinary skill in the art. Factors influencing the selected surface area of the membrane include the volume of sample treated, the concentration of the dephosphorylated material, and the desired throughput of the nanofiltration process.

The retentate after nanofiltration will preferably have a sialyloligosaccharide content of preferably about >1%, more preferably about >10%, more preferably >15%, and even more preferably, about >25%.

The retentate after nanofiltration will preferably have an orthophosphate content of preferably about <50% by weight, more preferably about <25% by weight, even more preferably about <10% by weight, and most preferably about <1% by weight.

In another embodiment of the invention, the isolated sialyloligosaccharide containing composition may be filtered again to separate any remaining enzymes from sialyloligosaccharides. In a preferred embodiment, this is accomplished through ultrafiltration. Techniques and equipment for the ultrafiltration of enzymes will be well known to those of ordinary skill in the art.

The present invention is also directed to a method of preparing a sialyloligosaccharide containing composition. The method comprises hydrolyzing a lactose component of a dairy stream comprising lactose and a sialyloligosaccharide; isolating a sialyloligosaccharide component; contacting the dairy stream with phytase; and adding said sialyloligosaccharide component to a composition.

Within the context of the present invention, a sialyloligosaccharide containing composition is any composition which contains a sialyloligosaccharide. Also, within the context of the present method, a sialyloligosaccharide component may be added to a composition or additional components may be added to a sialyloligosaccharide component to form the final composition.

Non-limiting examples of sialyloligosaccharide containing compositions which may be prepared include infant formula, cosmetic compositions, pharmaceutical compositions and food stuffs. Sialyloligosaccharides are found in human milk and incorporation of sialyloligosaccharides into an infant formula provides an infant formula with a composition which is more similar to human milk. There are also benefits resulting from the topical administration of sialyloligosaccharides to skin and accordingly cosmetic compositions containing sialyloligosaccharides are desired. Sialyloligosaccharides have been reported as useful in methods for treating arthritis and the treatment and prevention of gastric ulcers caused by Helicobacter pylori and accordingly preparation of pharmaceutical compositions containing sialyloligosaccharides is useful. Consumption of sialyloligosaccharides can be beneficial to neurological development, and therefore, a foodstuff comprising sialyloligosaccharides would be useful.

Sialyloligosaccharides, such as 3' sialyllactose, 6' sialyllactose, 6' sialyllactosamine, 3' sialyllactosamine and disialyllactose are useful as bacterial anti-adhesives, anti-infectives and as an additive for infant formula. The utility of sialic acid containing compositions is reported in U.S.

Pat. No. 5,270,462. Sialyllactose is also reported as being useful in a method for treating arthritis (U.S. Pat. No. 5,164,374). 3'-sialyllactose may be used to prevent and treat gastric ulcers caused by Helicobacter pylori.

The present invention is also directed to a composition comprising a sialyloligosaccharide, glucose and galactose, wherein glucose and galactose are present in a ratio of 0.9 to 1.1:1, preferably 0.95 to 1.05:1.

As a result of hydrolysis of lactose a dairy stream component containing sialyloligosaccharides, glucose and galactose is created in which glucose and galactose is present in nearly a 1:1 ratio, typically from 0.95 to 1.05:1. Such a composition may further comprise a β galactosidase enzyme, a phytase enzyme and/or lactose. β galactosidase enzyme, phytase enzyme and/or lactose may also be removed by methods disclosed herein.

The present invention is also directed to a method of producing glucose and galactose by hydrolysis of the lactose component of a dairy stream. Using the conditions described above for the hydrolysis of a lactose component of a dairy stream followed by isolation of a sialyloligosaccharide component, a method of producing glucose and galactose from a dairy stream is described. Isolation of glucose and galactose from a hydrolyzed dairy stream may be by filtration, such as nanofiltration techniques as described above. The method of producing glucose and galactose may further comprise isolation of a sialyloligosaccharide component resulting in a product stream comprising glucose and galactose and a product stream comprising a sialyloligosaccharide. The method of producing glucose and galactose may additionally comprise separation of glucose from galactose by conventional methods known to those of ordinary skill in the art resulting in a product stream comprising glucose and a product stream comprising galactose. Within the context of the present invention a product stream comprising glucose, a product stream comprising galactose, a product stream comprising glucose and galactose and a product stream comprising a sialyloligosaccharide will comprise at least about 60% by weight, preferably at least about 75% by weight, more preferably at least about 90% by weight, and even more preferably at least about 95% by weight of the stated component, percent by weight being based on the solids content of the product stream.

Other features of the invention will become apparent in the course of the following description of exemplary embodiments which are given for illustration of the invention and are not intended to be limiting thereof.

EXAMPLE 1

4,500 units of β galactosidase were added to ultrafiltered whey permeate, which contained approximately 0.45 g of lactose and 0.1 g 3' sialyllactose, in an aqueous medium at a pH of 5.5 at 37° C. After 60 minutes, the composition of the whey permeate was determined by analysis by HPLC on a BioRad HPX-87H column, to contain less than 1% of the original lactose content at >99 wt. % of the-original 3' sialyllactose content.

EXAMPLE 2

Separation of the glucose and galactose from the hydrolyzed whey permeate of Example 1 was accomplished by nanofiltration, at a pressure of 200–300 psig. The effectiveness of removal of solids is detailed below:

| Solids Present | # of diafiltrations to remove 80% solids | Average Removal Rate of Solids | Average Removal Rate of 3' Sialyllactose |
|---|---|---|---|
| glucose, galactose | 3–5 | 65–72% | <0.1% |

EXAMPLE 3

For comparative purposes, a whey permeate containing approximately 0.45 g of lactose and 0.1 g of 3' sialyllactose was subject to nanofiltration, using a Desal GE membrane at a pressure of 200–300 psig. The whey permeate was not hydrolyzed by treatment with a β-galactosidase enzyme. The effectiveness of removal of solids is detailed below:

| Solids Present | # of diafiltrations to remove 80% solids | Average Removal Rate of Solids | Average Removal Rate of 3' Sialyllactose |
|---|---|---|---|
| lactose | >7 | 25–40% | <0.1% |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of processing a dairy stream, the method comprising contacting a dairy stream comprising lactose and sialyloligosaccharide with phytase and β-galactosidase, thereby processing the dairy stream.

2. The method of claim 1, wherein a sialyloligosaccharide is isolated after treatment of the dairy stream with phytase.

3. The method of claim 1, wherein the dairy stream is contacted with both the phytase and the β-galactosidase in the same step.

4. The method of claim 1, wherein the dairy stream is contacted with the phytase and the β-galactosidase in separate steps.

5. A method of preparing a sialyloligosaccharide-containing composition from a dairy stream, the method comprising:
   i) hydrolyzing a lactose component of a dairy stream comprising lactose and a sialyloligosaccharide;
   ii) contacting the dairy stream with phytase;
   iii) isolating a sialyloligosaccharide containing component; therefrom and thereby preparing the sialytoligosaccharide containing composition.

6. The method of claim 5, wherein the hydrolyzing, contacting, and isolating are performed in any order provided that isolating the sialyloligosaccharide containing component is preceded by contacting the dairy stream with a phytase.

7. The method of claim 5, wherein the hydrolysis is conducted with a β-galactosidase enzyme.

8. The method of claim 5, wherein the sialyloligosaccharide component comprises a sialyloligosaccharide selected from the group consisting of 3' sialyllactose, 6' sialyllactose, 6' sialyllactosamine, 3' sialyllactosamine, disialyllactose and a mixture thereof.

9. The method of claim 5, wherein the phytase is immobilized on a support.

10. The method of claim 5, wherein the phytase is in an aqueous medium.

11. The method of claim 5, wherein the sialyloligosaccharide component is isolated by membrane filtration.

12. The method of claim 11, wherein the membrane filtration is nanofiltration.

13. A method of preparing a glucose and galactose containing composition from a dairy stream, the method comprising:

i) hydrolyzing a lactose component of a dairy stream comprising lactose and a sialyloligosaccharide;

ii) contacting the dairy stream with phytase;

iii) isolating a glucose and galactose containing component; therefrom and thereby preparing the glucose and galactose containing composition.

14. The method of claim 13, wherein the glucose and galactose containing composition comprises glucose and galactose in a ratio of about 0.95 to 1.05:1.

15. The method of claim 13, wherein the glucose and galactose containing composition is isolated by membrane filtration.

16. The method of claim 15, wherein the membrane filtration is nanofiltration.

* * * * *